(12) United States Patent
Njoku (10) Patent No.: US 9,339,531 B2
(45) Date of Patent: May 17, 2016

(54) RECOGNITION OF CYP2E1 EPITOPES

(75) Inventor: Dolores Benedicta Njoku, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 156 days.

(21) Appl. No.: 13/203,402

(22) PCT Filed: Feb. 26, 2010

(86) PCT No.: PCT/US2010/025570
§ 371 (c)(1),
(2), (4) Date: Aug. 25, 2011

(87) PCT Pub. No.: WO2010/099432
PCT Pub. Date: Sep. 2, 2010

(65) Prior Publication Data
US 2012/0040377 A1     Feb. 16, 2012

Related U.S. Application Data

(60) Provisional application No. 61/155,673, filed on Feb. 26, 2009.

(51) Int. Cl.
*A61K 39/00*     (2006.01)
*C07K 7/08*      (2006.01)
*C12N 9/02*      (2006.01)
*G01N 33/564*    (2006.01)

(52) U.S. Cl.
CPC .......... *A61K 39/0008* (2013.01); *C12N 9/0077* (2013.01); *G01N 33/564* (2013.01); *C12N 2770/24211* (2013.01); *G01N 2333/80* (2013.01); *G01N 2800/08* (2013.01); *G01N 2800/50* (2013.01)

(58) Field of Classification Search
None
See application file for complete search history.

(56) References Cited

U.S. PATENT DOCUMENTS

| 5,886,157 A * | 3/1999 | Guengerich et al. ......... 530/412 |
| 2003/0124601 A1 | 7/2003 | Nishimura et al. |
| 2003/0165843 A1* | 9/2003 | Shoshan et al. ................... 435/6 |
| 2006/0003942 A1 | 1/2006 | Tung et al. |
| 2008/0299094 A1 | 12/2008 | Oren |

OTHER PUBLICATIONS

Gene Bank, Cytochrome, P450, 2E1, Dec. 21, 2008.
Njoku et al., Clin. Vac. Immunology, vol. 13, No. 2, pp. 258-265 Dec. 31, 2006.
International Search Report (PCT/ISA/210).
Written Opinion (PCT/ISA/237).

* cited by examiner

*Primary Examiner* — Daniel E Kolker
*Assistant Examiner* — James Rogers
(74) *Attorney, Agent, or Firm* — Venable LLP; Keith G. Haddaway; Miguel A. Lopez (57) ABSTRACT

A critical epitope of human cytochrome P4502E1 (CYP2E1) associated with the development of hepatic autoimmune disease, including methods and kits for diagnosis and prognosis using the critical epitope as a biomarker for hepatic autoimmune disease.

4 Claims, 5 Drawing Sheets

FIGURE 1. CYP2E1 Peptides

| Epitope | CYP2E1 Amino Acids | Amino Acid Sequence | SEQ ID NO |
|---|---|---|---|
| JHDN1 | $Ser^2 - Leu^{19}$ | SALGVTVALLVWAAFLLL | 3 |
| JHDN2 | $Gln^{75} - Asp^{92}$ | QRMVVMHGYKAVKEALLD | 4 |
| JHDN3 | $His^{226} - Lys^{243}$ | HYLPGSHRKVIKNVAEVK | 5 |
| JHDN4 | $Ile^{377} - Ser^{394}$ | IFRGYLIPKGTVWPTLDS | 6 |
| JHDN5 | $Gly^{113} - Leu^{133}$ | GIIFNNGPTWKDIRRFSLTTL | 2 |
| JHDN6 | $Phe^{116} - Asn^{135}$ | FNNGPTWKDIRRFSLTTLRN | 7 |
| JHDN7 | $Gly^{119} - Met^{138}$ | GPTWKDIRRFSLTTLRNYGM | 8 |
| JHDN8 | $Trp^{122} - Lys^{140}$ | WKDIRRFSLTTLRNYGMGK | 9 |
| JHDN9 | $Ile^{125} - Ser^{145}$ | IRRFSLTTLRNYGMGKQGNES | 10 |

FIGURE 2

* indicate peptides that show inhibition in DO11.10 activation ; other peptides including JHDN 3, 5, 6, 7 &8 did not show inhibition were not included in the Figure.

RECOGNITION OF CYP2E1 EPITOPES

This application is a National Stage Application of International Application No. PCT/US2010/025570, filed Feb. 26, 2010, which claims priority to U.S. Provisional applications 61/155,673, filed Feb. 26, 2009, both of which are incorporated by reference herein in their entirety.

The work leading to the invention described and claimed herein was carried out using funds from the National Institutes of Health, grant no. R21DK075828. The U.S. Government has certain rights in the invention.

BACKGROUND OF THE INVENTION

1. Field of the Invention

The present invention relates to a critical epitope of human cytochrome P4502E1 (CYP2E1) associated with the development of hepatic autoimmune disease.

2. Background Information

Cytochrome P450 2E1 (CYP2E1) is a 493 amino acid enzyme (SEQ ID NO:1) involved in the monooxygenation of drugs and other xenobiotic agents. (1). CYP2E1 is a highly conserved protein in humans, and CYP2E1 is a known target of autoantibodies in several hepatic autoimmune diseases. (2). For example, autoantibodies to CYP2E1 have been identified in persons with drug induced liver injury (DILI). (2). DILI accounts for approximately 13% of acute liver failure in the United States and is the third most common cause of acute liver failure. (3). A type of DILI develops in susceptible individuals following administration of halogenated volatile anesthetics. (2, 3). Under physiological conditions, oxidative metabolism of the anesthetic produces trifluoroacetylchloride (TFA), which is a reactive metabolite that can covalently bind to and alter native liver proteins. (2, 3). The TFA-protein complexes, known as drug haptens, are novel autoantigens or hapten-autoantigen complexes (neoantigens) capable of eliciting allergic or autoimmune responses. (2, 3).

A second type of DILI is alcohol-induced liver disease. (2). Individuals chronically exposed to alcohol also develop autoantibodies to CYP2E1. (2).

Chronic viral infections are also known to induce autoimmunity directed to CYP2E1. (2). For example, chronic infection with hepatitis C virus (HCV) is known to induce autoimmune reactions. (2). Individuals with chronic hepatitis C (CHC) express decreased levels of CYP2E1, as measured by mRNA copy number (4), and CYP2E1 autoantibodies have been demonstrated in CHC patients (5). Indeed, a previous study has shown that CYP2E1 autoantibody levels correlate with the severity of necroinflammation in CHC patients after liver transplantation. (6). Thus, CYP2E1 plays a role in hepatic autoimmune disorders and there is a need to elucidate the mechanism of disease, including the formation of CYP2E1 autoantibodies.

DESCRIPTION OF THE INVENTION

The present invention is directed to a critical CYP2E1 epitope that contributes to the development of hepatic autoimmune diseases. Focusing on the anesthetic-induced DILI model of hepatic autoimmune disease, we hypothesized that anesthetic-induced DILI is mediated by autoimmune recognition of unique CYP2E1 epitopes in susceptible individuals. To test our hypothesis, we generated CYP2E1 peptides and tested the candidate epitopes for autoreactivity. Of nine candidates, only one epitope, $Gly^{113}$-$Leu^{133}$, was recognized by DILI-specific T cells and B cells. Therefore, T cells and B cells specific for the $Gly^{113}$-$Leu^{133}$ epitope mediate an autoimmune response that contributes to the development of hepatic autoimmune diseases.

The present invention provides novel polypeptides that are involved in the development of hepatic autoimmune diseases. Patients with hepatic autoimmune disease develop autoantibodies that are specific for the novel polypeptides. Polynucleotides comprising nucleic acid sequences encoding the polypeptides are also provided, as are vectors comprising the polynucleotides. Vectors comprising the polynucleotides and host cells comprising the polypeptides and/or polynucleotides are further provided.

The present invention also provides compositions comprising the polypeptides and/or polynucleotides described. Furthermore, methods for using the polypeptide and/or polynucleotide for identifying a mammalian subject at risk of developing hepatic autoimmune disease, diagnosing hepatic autoimmune disease in a mammalian subject, or monitoring the effect of therapy administered to a mammalian subject having hepatic autoimmune disease are provided, as well as kits for carrying out these methods.

1. DEFINITIONS

To facilitate an understanding of the present invention, a number of terms and phrases are defined below.

As used herein, the singular forms "a", "an", and "the" include plural forms unless the context clearly dictates otherwise. Thus, for example, reference to "a polypeptide" includes reference to more than one polypeptide.

The term "epitope" as used herein refers to that portion of an antigen capable of being recognized and specifically bound by a particular T cell or B cell. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

The terms "polypeptide," "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention, for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

"Polynucleotide," or "nucleic acid," are used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs, as well as other modifications known in the art.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those that have been purified to a degree that they are no longer in a form in which they are found in nature. In some embodiments, a polypeptide, polynucleotide, vector, cell, or composition which is isolated is substantially pure.

The term "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The term percent "sequence identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software are known in the art that may be used to obtain alignments of amino acid or nucleotide sequences. Non-limiting examples of sequence alignment softwares include Bestfit, NBLAST, XBLAST, Gapped BLAST, BLAST-2, WU-BLAST-2, ALIGN, ALIGN-2, or Megalign. Appropriate parameters for maximal alignment by a particular alignment software can be determined by one skilled in the art.

For example, the Bestfit program can determine the percentage sequence identity of a particular polynucleotide and a reference sequence (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482 489 (1981), to find the best segment of homology between two sequences. When using Bestfit or any other sequence alignment program to determine whether a particular sequence is, for instance, 95% identical to a reference sequence, the parameters are set such that the percentage of identity is calculated over the full length of the reference nucleotide sequence. Gaps in homology of up to 5% of the total number of nucleotides in the reference sequence are allowed.

"Conditions of high stringency," may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. An antibody can be of any the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity).

"Detectable moiety" or a "label" refers to a composition detectable by spectroscopic, photochemical, biochemical, immunochemical, or chemical means. For example, useful labels include $^{32}$P, $^{35}$S, fluorescent dyes, electron-dense reagents, enzymes (e.g., as commonly used in an ELISA), biotin-streptavidin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantify the amount of bound detectable moiety in a sample. Quantitation of the signal is achieved by, e.g., scintillation counting, densitometry, flow cytometry, or direct analysis by mass spectrometry of intact or subsequently digested peptides (one or more peptide can be assessed). Persons of skill in the art are familiar with techniques for labelling compounds of interest, and means for detection.

By "binding assay" is meant a biochemical assay wherein the biomarkers are detected by binding to an agent, such as an antibody, through which the detection process is carried out. The detection process may involve radioactive or fluorescent labels, and the like. The assay may involve immobilization of the biomarker, or may take place in solution. Techniques for carrying out such assays are well known in the art.

"Immunoassay" is an assay that uses an antibody to specifically bind an antigen (e.g., a marker). The immunoassay is characterized by the use of specific binding properties of a particular antibody to isolate, target, and/or quantify the antigen.

"Diagnostic" means identifying the presence or nature of a pathologic condition and includes identifying patients who are at risk of developing a specific disease or disorder. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "detection", "detecting" and the like, may be used in the context of detecting biomarkers, or of detecting a disease or disorder (e.g., when positive assay results are obtained). In the latter context, "detecting" and "diagnosing" are considered synonymous.

"At risk of" is intended to mean at increased risk of, compared to a normal subject, or compared to a control group, e.g., a patient population. Thus, a subject carrying a particular marker may have an increased risk for a specific disease or disorder, and be identified as needing further testing. "Increased risk" or "elevated risk" mean any statistically significant increase in the probability, e.g., that the subject has the disorder. The risk is preferably increased by at least 10%, more preferably at least 20%, and even more preferably at least 50% over the control group with which the comparison is being made. [Dolores: Are these % risks reasonable?]

The terms "subject", "patient" or "individual" generally refer to a human, although the methods of the invention are not limited to humans, and should be useful in other mammals (e.g., mice).

"Sample" is used herein in its broadest sense. A sample may comprise a bodily fluid including blood, serum, plasma, tears, aqueous and vitreous humor, spinal fluid, and saliva; a soluble fraction of a cell or tissue preparation, or media in which cells were grown; an organelle or membrane isolated or extracted from a cell or tissue; polypeptides, or peptides in solution or bound to a substrate; a cell; a tissue; a tissue print; a fingerprint, skin or hair; fragments and derivatives thereof. Subject samples usually comprise derivatives of blood products, including blood, plasma and serum.

2. POLYPEPTIDES AND POLYNUCLEOTIDES

The present invention provides a polypeptide having an amino acid sequence comprising amino acids from about 113 to 133 of CYP2E1 (SEQ ID NO:2). In one embodiment, the polypeptide has at least 80% sequence identity, more preferably at least 90% sequence identity, and still more preferably 95%, 96%, 97%, 98%, or 99% sequence identity to SEQ ID NO:2. In another embodiment, the polypeptide consists of 21 to 30 amino acid residues, comprising SEQ ID NO:2. In certain embodiments, the polypeptide is isolated. In a further embodiment, the polypeptide is substantially pure.

In another aspect, the invention is a polynucleotide having a nucleic acid sequence that encodes the amino acids from about 113 to 133 of CYP2E1. In one embodiment, the polynucleotide encodes the amino acids of a polypeptide that has 80%, 95%, 96%, 97%, 98% or 99% sequence identity to SEQ ID NO:2. In another embodiment, the polynucleotide has at least 90% sequence identity, and more preferably at least 95%, 96%, 97%, 98%, or 99% sequence identity to the above described polynucleotides. In some embodiments, the polynucleotide consists of 63 to 90 nucleotide bases. In certain embodiments, the polynucleotide is isolated. In a further embodiment, the polynucleotide is substantially pure.

In a further aspect, the present invention provides a polynucleotide that comprises a nucleic acid that is complementary over its entire length, or that hybridizes to a polynucleotide encoding SEQ ID NO:4 under conditions of high stringency.

The polypeptides described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding the polypeptide of interest.

In some embodiments, a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

In some embodiments, the polynucleotides comprise the coding sequence for the polypeptide of interest fused in the same reading frame to nucleotides that aid, for example, in expression and secretion of the polypeptide from a host cell (e.g., a leader sequence that functions as a secretory sequence for controlling transport of a polypeptide from the cell). The resultant protein product has a leader sequence that can be cleaved by the host cell to yield the polypeptide of interest.

In some embodiments, the polynucleotides comprise the coding sequence for the polypeptide of interest fused in the same reading frame to a marker sequence that allows for purification of the encoded polypeptide. Marker sequences useful for protein purification are known in the art. For example, in a bacterial host, the marker sequence can be a hexahistidine tag (SEQ ID NO:11) supplied by a pQE-9 vector. In a mammalian host, the marker sequence can be a hemagglutinin (HA) tag derived from the influenza hemagglutinin protein.

3. VECTORS AND HOST CELLS

The present invention also relates to recombinant expression vectors that comprise the isolated nucleic acid molecules of the present invention, host cells that are genetically engineered with the recombinant vectors, and production of polypeptides of the present invention by recombinant techniques.

Recombinant expression vectors are replicable DNA constructs that have synthetic or cDNA-derived fragments encoding a polypeptide of the present invention, operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence that is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor that participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations are known in the art. For example, nonlimiting examples of useful expression vectors for eukaryotic hosts include vectors comprising expression control sequences from SV40, bovine papilloma virus, adenovirus, and cytomegalovirus. Nonlimiting examples of useful expression vectors for bacterial hosts include known bacterial plasmids, such as pCR 1, pBR322, pMB9, and their derivatives, and wider host range plasmids, such as M13 and filamentous single-stranded DNA phages.

Suitable host cells for expression of the polypeptides described herein include prokaryotes, yeast, insect, or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are known in the art.

Various mammalian or insect cell culture systems are also advantageously employed to express recombinant protein. Expression of recombinant proteins in mammalian cells can be performed because such proteins are generally correctly folded, appropriately modified and completely functional. Nonlimiting examples of suitable mammalian host cell lines include the COS-7 lines of monkey kidney cells, L cells, C127, 3T3, Chinese hamster ovary (CHO), HeLa, and BHK cell lines. Mammalian expression vectors can comprise non-transcribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are also known in the art.

The proteins produced by a transformed host can be purified according to any suitable method. Standard methods include chromatography (e.g., ion exchange, affinity, and sizing column chromatography), centrifugation, differential solubility, or by any other standard technique for protein purification. Affinity tags such as hexahistidine (SEQ ID NO:11), maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

4. ASSAYS AND DIAGNOSTICS

The present invention also provides compositions comprising the polynucleotide and/or polypeptide as described herein. The compositions can be used in in vitro laboratory assays known in the art. Nonlimiting examples of methods that use the composition include generating monoclonal and polyclonal antibodies; detecting the interaction of the claimed polypeptide and/or polynucleotide with other biomolecules, such as intracellular proteins (e.g., transcription factors), antibodies, etc.; assessing drug toxicity (e.g., metabolic, proteomic, and transcriptional assays); and testing patient samples (e.g., lymphocyte transformation assay).

Additionally, the present invention provides a method of identifying a mammalian subject at risk for developing hepatic autoimmune disease. In some embodiments, the method comprises testing a biological sample from the patient for the presence of a polynucleotide or polypeptide as described herein. The presence of the claimed polypeptide or polynucleotide is indicative of increased risk of the patient for developing hepatic autoimmune disease.

Although susceptible individuals exposed to halogenated volatile anesthetics produce CYP2E1-specific autoantibodies, exposed susceptible individuals do not necessarily develop liver disease. We have previously shown that susceptible individuals who develop anesthetic-induced DILI have elevated levels of CYP2E1-specific IgG4 autoantibodies. (3).

In contrast, exposed susceptible individuals who develop CYP2E1-specific IgG1 autoantibodies remain healthy. (3). Therefore, pathogenesis in hepatic autoimmune disease is associated with the emergence of IgG4 autoantibodies.

The present invention provides a method for diagnosing a patient with hepatic autoimmune disease. In some embodiments, the method comprises testing a biological sample from a patient for the presence of IgG4 autoantibodies that are specific for the $Gly^{113}$-$Leu^{133}$ epitope of CYP2E1. The presence of the IgG4 autoantibodies is indicative that the patient has hepatic autoimmune disease. In some embodiments, the IgG4 autoantibody levels are used to determine the stage and severity of the hepatic autoimmune disease. In some embodiments, the IgG4 autoantibody levels are used to monitor the effect of therapy administered to a patient.

The presence of the biomarkers, i.e., the polypeptide, the polynucleotide, or the $Gly^{113}$-$Leu^{133}$ specific IgG4 autoantibody, can be detected by any suitable means known to those of skill in the art. Nonlimiting examples of methods for detecting the biomarkers include using a protein assay, a binding assay, or an immunoassay. Biomarkers may also be identified as peaks using Mass Spectroscopy, or as gel bands using, for example, size exclusion chromatography.

Biological samples suitable for testing include tissue samples, e.g., whole blood, or fractions thereof such as plasma and serum; cells; urine; saliva; and inter- and intracellular fluid samples. Means of obtaining suitable biological samples are known to those of skill in the art.

Also provided are kits for carrying out the methods described herein. In some embodiments, the kit may comprise one or more reagents, including an antibody (or a chemical moiety) that binds to a biomarker. The kit may also comprise a labeled binding partner to any antibody present in the kit. If no labeled binding partner is provided, each antibody itself can be labeled with a detectable marker, e.g., a chemiluminescent, enzymatic, fluorescent, or radioactive moiety.

In another embodiment, the biomarker is directly detected using mass spectrometry. In this embodiment, the kit contains an antibody that binds to the biomarker. The antibody is coupled to a matrix (e.g., in a small column or packed into an end of a pipette tip) such that the biomarker is enriched and then analyzed by mass spectrometry.

In a further embodiment, the kit may comprise a polypeptide as described herein, a polynucleotide as described herein, or a complement thereof. The kit may also comprise a labeled binding partner to any polypeptide, polynucleotide, or complement present in the kit. If no labeled binding partner is provided, each polypeptide, polynucleotide, or complement itself can be labeled with a detectable marker, e.g., a chemiluminescent, enzymatic, fluorescent, or radioactive moiety.

Kits of the present invention may contain a plurality of antibodies so that multiple biomarkers can be assessed simultaneously.

Optionally, the kit can include instructions for taking a sample from the mammalian subject (e.g., body fluid), and using the kit to identify a mammalian subject at risk of developing hepatic autoimmune disease, diagnosing hepatic autoimmune disease in a mammalian subject, or monitoring the effect of therapy administered to a mammalian subject having hepatic autoimmune disease.

Embodiments of the present invention can be further defined by reference to the following non-limiting examples, which describe the methodology employed to identify and characterize a CYP2E1 epitope that is the target of autoantibodies in hepatic autoimmune disease. It will be apparent to those skilled in the art that many modifications, both to materials and methods, may be practiced without departing from the scope of the present disclosure.

EXAMPLES

It is understood that the examples and embodiments described herein are for illustrative purposes only and that various modifications or changes in light thereof will be suggested to persons skilled in the art and are to be included within the spirit and purview of this application.

Example 1

A Mouse Model for Hepatic Autoimmune Disease

We developed a hapten-induced mouse model of hepatic autoimmune disease by immunizing Balb/C mice with syngeneic S100 liver proteins covalently coupled to trifluoroacetylchloride (TFA-S100). TFA is a reactive metabolite of halogenated volatile anesthetics that binds to and alters liver proteins in patients with anesthetic-induced DILI. As such, TFA-S100 is a model antigen for the neoantigens that are formed in patients with anesthetic-induced DILI.

Mice

Inbred Balb/c mice, 8 to 10 weeks old, were obtained and maintained under pathogen-free conditions.

Preparation of Hepatic S100

The hepatic cytosolic S100 fraction was isolated from female BALB/c mice using the methods of Lohse et al. (1990) (7). Briefly, mice were killed by cervical dislocation. After the liver was exposed and the inferior vena cava cut, the liver was perfused for 10 min with cold PBS (Biofluids BSI, Rockville, Md.) by cannulating the portal vein with a 24-gauge angiocatheter. Livers were pooled, weighed, minced, and homogenized with four times weight per volume of homogenizing buffer (Sucrose, 250 mM; Tris, 10 mM; EDTA, 1 mM; pH 7.4; JT Baker, Phillipsburg, N.J.) supplemented with protease inhibitors (Completek protease inhibitor cocktail tablets, Roche Applied Science, Indianapolis, Ind.). The liver homogenate was centrifuged at 1500 g for 10 min using a Sorvall RC Plus (rotor: Sorvall SS-34) at 4° C. The supernatant was collected and centrifuged for 1 h at 100 g using the Beckman L8-80 M ultracentrifuge (rotor: SW40Ti). The resulting supernatant contains the S100 cytosolic fraction.

Preparation of Haptenated Cytosolic S100 (TFA-S100)

To prepare the TFA-S100 immunogen, the protein concentration of the S100 cytosolic fraction was determined using a BCA Protein Assay Kit (Pierce, Rockford, Ill.). Trifluoroacetylation of the e-amino groups of lysine residues of S100 was performed according to the procedures of Goldberger and Anfinsen (1963) (8) and Satoh et al. (1985) (9). All steps were performed in a fume hood. Cytosolic S100 (2 mg) was dissolved in distilled water (dH2O). The pH was adjusted to 10 with 1 N potassium hydroxide (KOH; J T Baker). The reaction was initiated by adding S-ethyltrifluoroacetylthioacetate (SETFA; J T Baker) 7.8 mM/mg of S100. The pH was maintained from 9.9 to 10.0 with 1 N KOH for approximately 1 h. The reaction mixture was dialyzed for 72 h against 4 L of dH2O with three changes per day using Slide-A-Lyzer Cassettes® (Pierce). After dialysis, the final volume of TFA-S100 was recorded, snap frozen, and stored at −80° C.

Induction of Hepatic Autoimmune Disease in BALB/c Mice

To induce hepatic autoimmune disease, BALB/c mice (10 mice/group) were immunized subcutaneously (s.c.) with 200 µg of syngenic TFA-S100 (1 mg/mL in PBS, Biofluidsk) emulsified in an equal volume of CFA (Difco Bacto Complete Freund's Adjuvant H37 Ra, Fisher Scientific, Pittsburgh, Pa.)

at the base of the neck, and 500 ng of pertussis toxin (PT) (List Biologicals, Campbell, Calif.) was administered intramuscularly in the right hind flank at day 0. One week after the original immunization, mice received 200 µg of syngenic TFA-S100 (1.0 mg/mL) emulsified in an equal volume CFA s.c. at the base of the tail (TFA-S100 group).

The immunized mice show an organ-specific inflammatory response to the haptenated liver proteins. (10). Serum ALT levels, a marker of hepatic cell damage, is increased following immunization with TFA-S100, and hepatic inflammation peaks by 3 weeks after immunization. (10). Hepatic inflammatory infiltration (i.e., neutrophils, mast cells, and eosinophils) following TFA-S100 immunization is characteristic of infectious and drug-induced hepatic autoimmune disease, and the immunized mice also produce IgG autoantibodies specific for TFA-S100. (10). Furthermore, the immunized mice produce increased levels of Th1- and Th2-type cytokines in the spleen, indicating that immunization with the TFA hapten globally up-regulates the immune response to S100 in BALB/c mice. (10).

As the hapten-induced mouse model of hepatic autoimmune disease produces an overall immune response to a TFA hapten that is distinct and measurable, this mouse model is a useful tool for characterizing antigenic epitopes that are involved in the development of hepatic autoimmunity diseases.

Example 2

Figure 1:
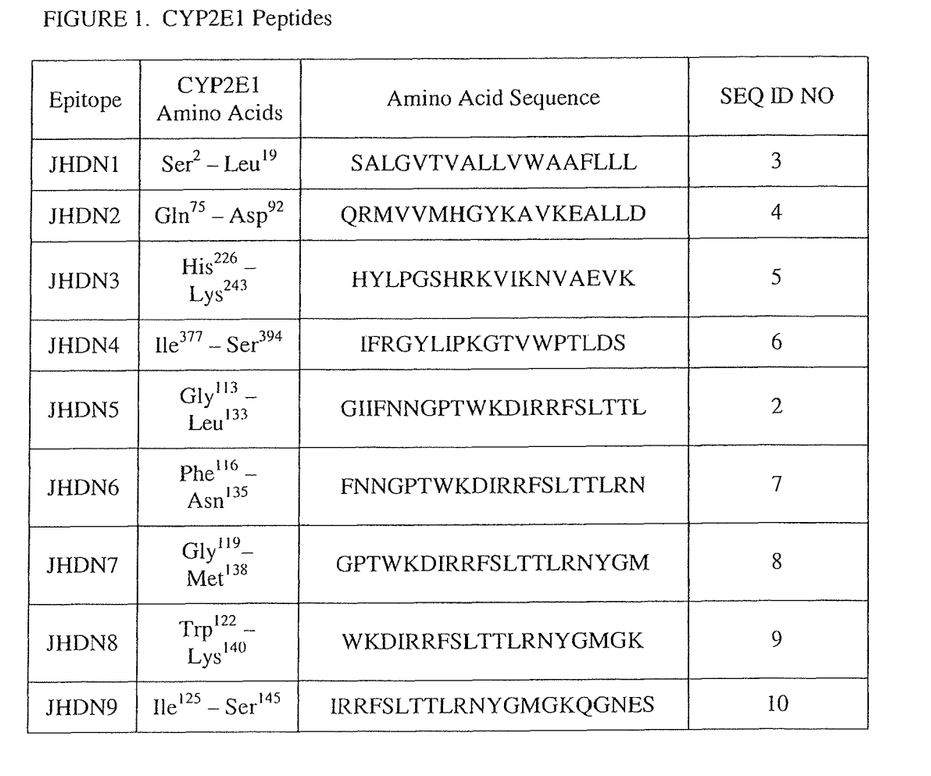
FIG. 1. Putative CYP2E1 epitopes.

Identification of a CYP2E1 Epitope that is Involved in the Development of Hepatic Autoimmune Disease Selection of Candidate CYP2E1 Epitopes In order to take advantage of the mouse model of hepatic autoimmunity disease, we wanted to identify putative antigenic epitopes of CYP2E1 that are found in both human and mouse CYP2E1. Using the Rankprep software, which predicts antigens capable of binding MHC molecules, we selected nine peptides for further study (FIG. 1).

Epitope Binding to Mouse MHC II

Using the well known model system of 1-Ad DO11.10 T cell hybridomas+F LS102.9 activation and competitive inhibition of the ovalbumin (OVA) 323-329 peptide, we tested the ability of the nine candidate epitopes to bind mouse MHC II.

Figure 2:
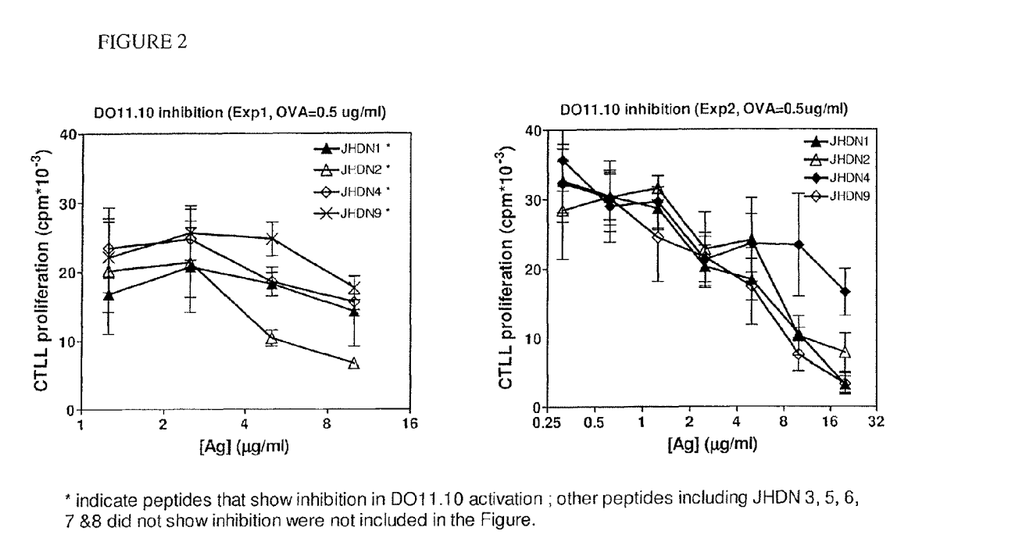
FIG. 2. Competitive inhibition assay to assess MHC II binding. 1-Ad DO11.10 T cell hybridomas were cultured in the presence of 0.5 ug/ml OVA 323-329 peptide and varying concentrations of JHDN1, JHDN2, JHDN4, or JHDN9. CTLL-2 cells were added, and CTLL-2 proliferation was measured by $^3$H incorporation. JHDN1, JHDN2, JHDN4, and JHDN9 competitively bound the I-Ad hybridoma, resulting in decreased proliferation of CTLL-2 cells.

I-Ad hybridomas engaged by the OVA 323-329 peptide produce IL-2. Production of IL-2 can be assed by adding and measuring the proliferation of CTLL-2 cells, i.e., cytotoxic T lymphocytes, because CTLL-2 cells require IL-2 for proliferation. Cultures containing I-Ad hybridomas and 0.5 µg/ml of OVA peptide were set up in complete media. CTLL-2 cells were added to the cultures and proliferation was assessed by measuring $^3$H thymidine incorporation. Of the nine epitopes tested, JHDN1, JHDN2, JHDN4, and JHDN9 competitively bound the 1-Ad hybridoma (FIG. 2). Thus, our results show that the JHDN1, JHDN2, JHDN4, and JHDN9 epitopes are able to bind mouse MHC II of the I-Ad haplotype.

Serum Assays for Antibodies to JHDN1

Using an ELISA assay, we determined whether JHDN1, JHDN2, JHDN4, and JHDN9 are recognized by persons with autoantibodies to CYP2E1. We included JHDN5 and JHDN6 in these experiments, because the JHDN5 and JHDN6 epitopes are located near the active site of CYP2E1.

Human sera was obtained from individuals without exposure to general anesthetics (Control), anesthesiologists with low or moderate general anesthetic exposure (JHU), pediatric anesthesiologists with high exposure to general anesthetics (SPA), and patients with anesthetic-induced DILI (AH). Immulon 4HB plates were coated overnight with 0.5 µg/100 µL of a candidate epitope. 1:100 dilution of human sera was added as the first antibody, followed by an anti-human IgG secondary antibody conjugated to alkaline phosphatase (AP). AP product formation was determined at 405 nm using an automatic plate reader.

Figure 3:
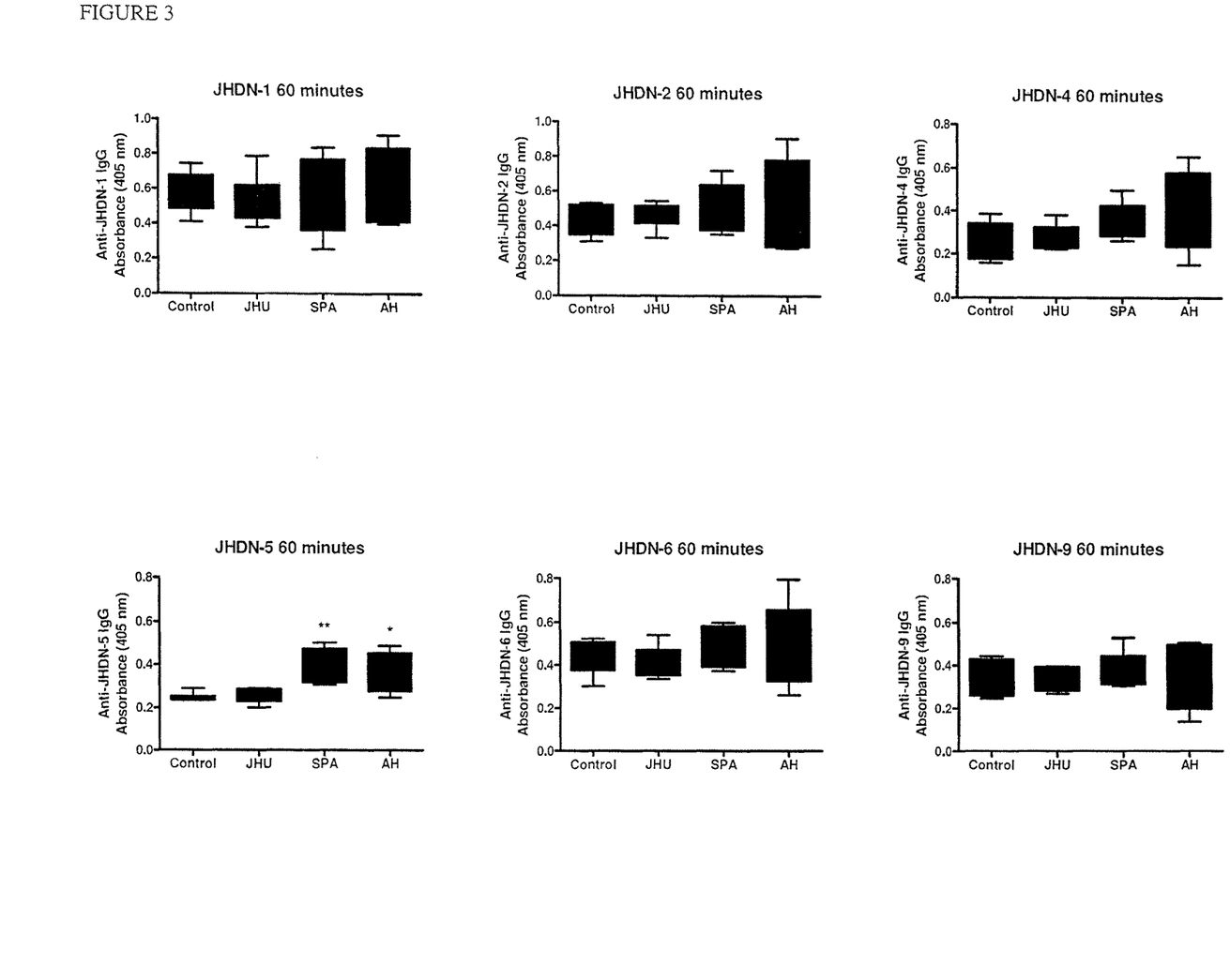
FIG. 3. Serum assays for detecting autoantibodies specific for candidate CYP2E1 epitopes. Sera obtained from patients with anesthetic-induced DILI (AH), individuals with high exposure to general anesthetics without DILI (SPA), individuals with moderate or low exposure to general anesthetics (JHU), and normal individuals (Control) were tested for autoantibodies that recognize the JHDN1, JHDN2, JHDN4, JHDN5, JHDN6, and JHDN9 epitopes. AH: anesthetic hepatitis patients, SPA: pediatric anesthesiologists, JHU: general anesthesiologists, CON: control patients without exposure to anesthetics.

Of the epitopes tested, only JHDN5 showed immunoreactivity to the human sera (FIG. 3). Our results indicate that patients with anesthetic induced DILI as well as persons with high exposure to general anesthetics without DILI have autoantibodies specific for JHDN5.

Splenocyte Proliferation Assay

We then determined whether splenocytes obtained from TFA-S100 immunized mice proliferated in response to JHDN1, JHDN2, JHDN4, JHDN5 and JHDN9.

As described above, BALB/c mice were immunized with TFA-S100. Splenocytes from BALB/c mice immunized with S100 in CFA plus PT or CFA and PT alone were used as controls. Splenocyte isolation was performed using basic immunological techniques. Briefly, spleens were harvested two weeks after immunization. Spleens were mashed between two frosted glass slides, and tissue debris was removed by filtering the sample through a 70 µm cell strainer. The remaining cells were washed with sterile phosphate buffered saline/2% fetal calf serum (PBS/2% FCS) and centrifuged at 1500 rpm for 10 minutes using a refrigerated desktop centrifuge. Red cells were lysed using ACK lysing buffer. The remaining cells were washed with RPMI-10% HEPES and filtered through a 70 µm cell strainer. The splenocytes were stored in RPMI complete media with 10% FCS (RPMI-10) at a final concentration of 2.5 million cells per 1 mL of media.

For the proliferation assays, $2.5 \times 10^5$ splenocytes (100 µl) were added to each well of a 96 well plate with 0.1 µg/mL, 0.5 µg/mL, or 1 µg/mL of a candidate epitope. As controls, media or concanavalin A (Con A) were also tested in the proliferation assays. Plates were incubated for 3 days at 37° C., 5% $CO_2$, 95% air (humidified). Six to 18 hours prior to the 72 hour time point, the splenocytes were pulsed with 1 µCi/well $^3$H thymidine (0.25 mCi/0.25 ml stock). Specifically, a 1:10 dilution (0.1 mCi/ml) of the $^3$H thymidine stock solution is made by adding 200 µl of $^3$H thymidine stock solution to 1800 µl of sterile RPMI. 10 µl (1 µCi) of diluted $^3$H thymidine was pipetted into each well. The cells were incubated for 48 hours. After incubation, cells were placed in −20° C. for up to 45 minutes to stop the incorporation of $^3$H thymidine into proliferating cells. The splenocytes were analyzed and $^3$H incorporation, an indicator of cellular proliferation, was measured.

Figure 4A:
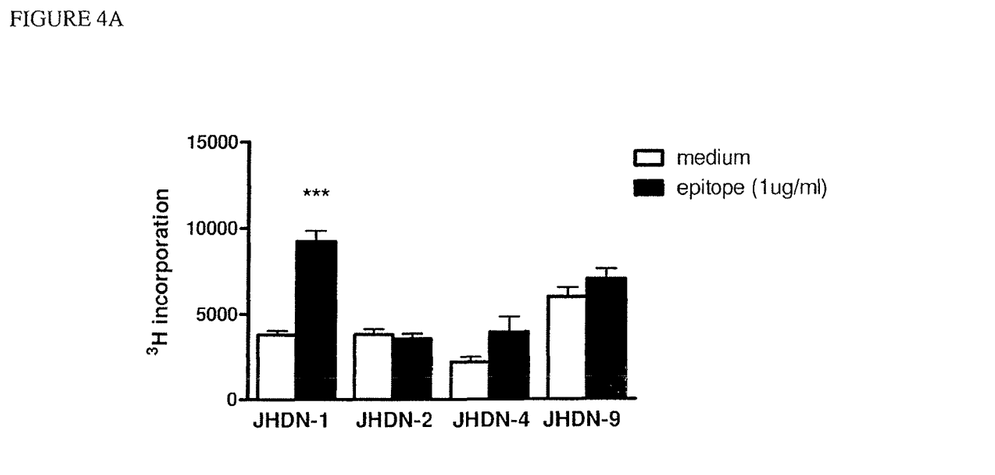
FIG. 4. Splenocyte proliferation assays with candidate CYP2E1 epitopes. Splenocytes were obtained from mice immunized with TFA-S100 and treated with JHDN1, JHDN2, JHDN4, JHDN5, or JHDN9. (A) shows the level of $^3$H incorporation observed with the JHDN1, JHDN2, JHDN4, and JHDN9 epitopes. (B) shows the proliferation observed with the JHDN5 epitope as measured using a proliferation index. Proliferation indices of ≥2 were determined to be significantly different from cultures incubated in media alone.
Figure 4B:
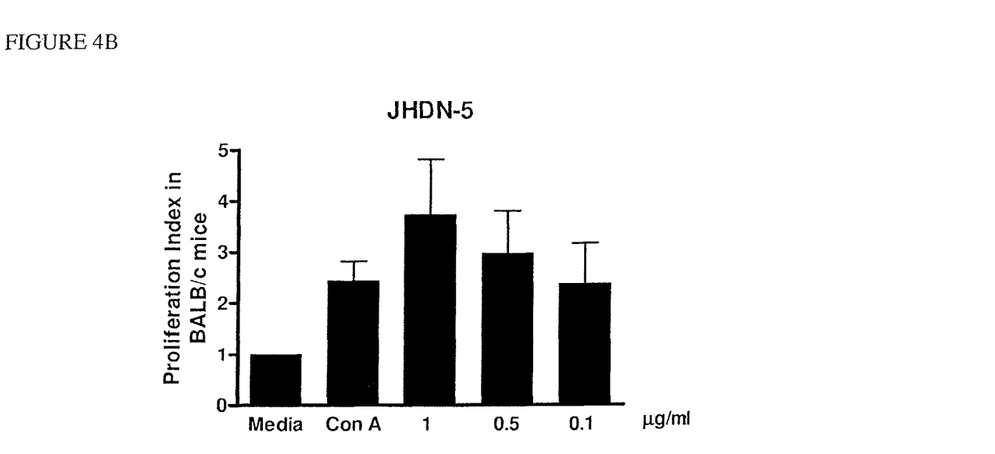

Proliferation assays with JHDN1, JHDN2, JHDN4, JHDN5 and JHDN9 were performed in triplicate, with splenocytes obtained from approximately 5 mice per experimental group. Our results show that JHDN1 (FIG. 4A) and JHDN5 (FIG. 4B) were able to activate T cells in the hapten-induced mouse model of hepatic autoimmune disease.

JHDN5 is the only candidate epitope that is recognized by DILI-specific T cells (as assessed using the hapten-induced mouse model of hepatic autoimmune disease) and B cells. Therefore, our results indicate that the JHDN5 epitope, i.e., Gly$^{113}$-Leu$^{133}$ of CYP2E1, is an antigenic epitope associated with the development of hepatic autoimmune disease.

Example 3

Production of JHDN5 Specific Antibodies

We used ClonaCell®-HY technology to develop hybridomas that would recognize the JHDN5 epitope. We used this technology because it specializes in isolating hybridomas to minor antigens.

BALB/c mice were immunized with JHDN-5 emulsified in CFA. The mice received a total of four immunizations weekly. As per the manufacturer's instructions, we fused cells from the immunized mice, and selected clones were harvested after seven to ten days. Individual hybridomas were selected, grown in the provided media, and the media subsequently tested for IgG to JHDN5. The level of JHDN5 specific antibodies produced by an individual hybridoma was determined using the above described ELISA assay, with the JHDN5 epitope as the target antigen.

Figure 5:
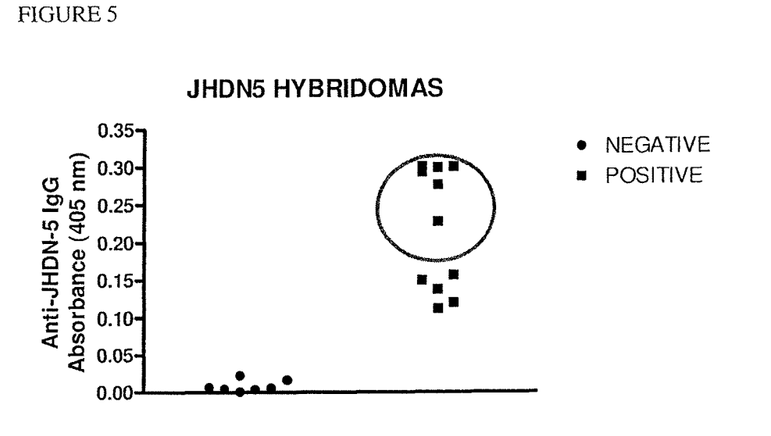
FIG. 5. Antibody production in JHDN5 specific hybridomas. Hybridomas that recognize the JHDN5 epitope were produced using ClonaCell®-Hy technology. Individual hybridomas were selected and tested for IgG to the JHDN5 epitope using an ELISA assay with the JHDN5 epitope as the target antigen.

Our hybridomas produced measurable levels of JHDN5 specific IgG (OD>0.200) (FIG. 5). The antibodies produced by the hybridomas can be used in various research and clinical methods, including in vitro laboratory assays and diagnostic assays.

All publications cited herein are hereby incorporated by reference in their entirety.

References cited herein are listed below for convenience:

(1) Porubsky P R, Meneely K M, Scott E E. Structures of human cytochrome P-450 2E1. Insights into the binding of inhibitors and both small molecular weight and fatty acid substrates. J Biol Chem 2008; 283(48):33698-707.

(2) Obermayer-Straub P, Strassburg C P, Manns M P. Target proteins in human autoimmunity: cytochromes P450 and UDP-glucuronosyltransferases. Can J Gastroenterol 2000 May; 14(5):429-39.

(3) Njoku D B, Mellerson J L, Talor M V, Kerr D R, Faraday N R, Outschoorn I, Rose N R. Role of CYP2E1 Immunoglobulin G4 Subclass Antibodies and Complement in Pathogenesis of Idiosyncratic Drug-Induced Hepatitis. Clin Vaccine Immun 2006; 13(2):258-65.

(4) Nakai K, Tanaka H, Hanada K, Ogata H, Suzuki F, Kumada H et al. Decreased expression of cytochromes P450 1A2, 2E1, and 3A4 and drug transporters Na$^+$-taurocholate-cotransporting polypeptide, organic cation transporter 1, and organic anion-transporting peptide-C correlates with the progression of liver fibrosis in chronic hepatitis C patients. Drug Metab Dispos 2008; 36(9):1786-93.

(5) Vidali M, Occhino G, Ivaldi A, Serino R, Moia S, Alchera E et al. Detection of autoantibodies against cytochrome P4502E1 (CYP2E1) in chronic hepatitis C. J Hepatol 2007; 46(4): 605-12.

(6) Rigamonti C, Vidali M, Donato M F, Sutti S, Occhino G, Ivaldi A et al. Serum autoantibodies against cytochrome P450 2E1 (CYP2E1) predict severity of necroinflammation of recurrent hepatitis C. Am J Transplant 2009; 9(3): 601-9.

(7) Lohse A W, Manns M, Dienes H P, Meyer zum Biischenfelde K H, Cohen I R. Experimental autoimmune hepatitis: disease induction, time course and T-cell reactivity. Hepatology 1990; 11(1):24-30.

(8) Goldberger R, Anfinsen, C. The reversible masking of amino groups in ribonuclease and its possible usefulness in the synthesis of the protein. Biochemistry 1963; 1(3):401-5.

(9) Satoh H, Fukuda Y, Anderson D K, Ferraris V J, Gillette J R, Pohl L R. Immunological studies on the mechanism of halothane-induced hepatotoxicity: immunohistochemical evidence of trifluoroacetylated hepatocytes. J Pharmacol Exp Ther 1985; 233(3):857-62.

(10) Njoku D B, Talor M V, Fairweather D, Frisancho-Kiss S, Odumade O A, Rose N R. A novel model of drug hapten-induced hepatitis with increased mast cells in the BALB/c mouse. Exp Mol Pathol 2005; 78(2):87-100.

I claim:

1. An isolated cDNA which encodes a purified CYP2E1 epitope comprising the sequence of SEQ ID NO: 2, wherein the epitope is 21-30 amino acids in length.

2. An isolated cDNA having at least 90% sequence identity to the isolated cDNA of claim 1.

3. The isolated cDNA of claim 2, wherein the isolated cDNA has at least 95% sequence identity to the isolated cDNA of claim 1.

4. The isolated cDNA of claim 2, wherein the isolated cDNA has at least 99% sequence identity to the isolated cDNA of claim 1.

* * * * *

SEQUENCE LISTING

```
<160> NUMBER OF SEQ ID NOS: 11

<210> SEQ ID NO 1
<211> LENGTH: 493
<212> TYPE: PRT
<213> ORGANISM: Homo sapiens

<400> SEQUENCE: 1

Met Ser Ala Leu Gly Val Thr Val Ala Leu Leu Val Trp Ala Ala Phe
1               5                   10                  15

Leu Leu Leu Val Ser Met Trp Arg Gln Val His Ser Ser Trp Asn Leu
            20                  25                  30
```

```
Pro Pro Gly Pro Phe Pro Leu Pro Ile Ile Gly Asn Leu Phe Gln Leu
        35                  40                  45
Glu Leu Lys Asn Ile Pro Lys Ser Phe Thr Arg Leu Ala Gln Arg Phe
     50                  55                  60
Gly Pro Val Phe Thr Leu Tyr Val Gly Ser Gln Arg Met Val Val Met
 65                  70                  75                  80
His Gly Tyr Lys Ala Val Lys Glu Ala Leu Leu Asp Tyr Lys Asp Glu
                 85                  90                  95
Phe Ser Gly Arg Gly Asp Leu Pro Ala Phe His Ala His Arg Asp Arg
                100                 105                 110
Gly Ile Ile Phe Asn Asn Gly Pro Thr Trp Lys Asp Ile Arg Arg Phe
                115                 120                 125
Ser Leu Thr Thr Leu Arg Asn Tyr Gly Met Gly Lys Gln Gly Asn Glu
        130                 135                 140
Ser Arg Ile Gln Arg Glu Ala His Phe Leu Leu Glu Ala Leu Arg Lys
145                 150                 155                 160
Thr Gln Gly Gln Pro Phe Asp Pro Thr Phe Leu Ile Gly Cys Ala Pro
                165                 170                 175
Cys Asn Val Ile Ala Asp Ile Leu Phe Arg Lys His Phe Asp Tyr Asn
            180                 185                 190
Asp Glu Lys Phe Leu Arg Leu Met Tyr Leu Phe Asn Glu Asn Phe His
        195                 200                 205
Leu Leu Ser Thr Pro Trp Leu Gln Leu Tyr Asn Asn Phe Pro Ser Phe
        210                 215                 220
Leu His Tyr Leu Pro Gly Ser His Arg Lys Val Ile Lys Asn Val Ala
225                 230                 235                 240
Glu Val Lys Glu Tyr Val Ser Glu Arg Val Lys Glu His His Gln Ser
                245                 250                 255
Leu Asp Pro Asn Cys Pro Arg Asp Leu Thr Asp Cys Leu Leu Val Glu
            260                 265                 270
Met Glu Lys Glu Lys His Ser Ala Glu Arg Leu Tyr Thr Met Asp Gly
        275                 280                 285
Ile Thr Val Thr Val Ala Asp Leu Phe Phe Ala Gly Thr Glu Thr Thr
    290                 295                 300
Ser Thr Thr Leu Arg Tyr Gly Leu Leu Ile Leu Met Lys Tyr Pro Glu
305                 310                 315                 320
Ile Glu Glu Lys Leu His Glu Glu Ile Asp Arg Val Ile Gly Pro Ser
                325                 330                 335
Arg Ile Pro Ala Ile Lys Asp Arg Gln Glu Met Pro Tyr Met Asp Ala
                340                 345                 350
Val Val His Glu Ile Gln Arg Phe Ile Thr Leu Val Pro Ser Asn Leu
            355                 360                 365
Pro His Glu Ala Thr Arg Asp Thr Ile Phe Arg Gly Tyr Leu Ile Pro
    370                 375                 380
Lys Gly Thr Val Val Val Pro Thr Leu Asp Ser Val Leu Tyr Asp Asn
385                 390                 395                 400
Gln Glu Phe Pro Asp Pro Glu Lys Phe Lys Pro Glu His Phe Leu Asn
                405                 410                 415
Glu Asn Gly Lys Phe Lys Tyr Ser Asp Tyr Phe Lys Pro Phe Ser Thr
                420                 425                 430
Gly Lys Arg Val Cys Ala Gly Glu Gly Leu Ala Arg Met Glu Leu Phe
            435                 440                 445
```

-continued

Leu Leu Leu Cys Ala Ile Leu Gln His Phe Asn Leu Lys Pro Leu Val
            450                 455                 460

Asp Pro Lys Asp Ile Asp Leu Ser Pro Ile His Ile Gly Phe Gly Cys
465                 470                 475                 480

Ile Pro Pro Arg Tyr Lys Leu Cys Val Ile Pro Arg Ser
                485                 490

<210> SEQ ID NO 2
<211> LENGTH: 21
<212> TYPE: PRT
<213> ORGANISM: Homo sapiens

<400> SEQUENCE: 2

Gly Ile Ile Phe Asn Asn Gly Pro Thr Trp Lys Asp Ile Arg Arg Phe
1               5                   10                  15

Ser Leu Thr Thr Leu
            20

<210> SEQ ID NO 3
<211> LENGTH: 18
<212> TYPE: PRT
<213> ORGANISM: Homo sapiens

<400> SEQUENCE: 3

Ser Ala Leu Gly Val Thr Val Ala Leu Leu Val Trp Ala Ala Phe Leu
1               5                   10                  15

Leu Leu

<210> SEQ ID NO 4
<211> LENGTH: 18
<212> TYPE: PRT
<213> ORGANISM: Homo sapiens

<400> SEQUENCE: 4

Gln Arg Met Val Val Met His Gly Tyr Lys Ala Val Lys Glu Ala Leu
1               5                   10                  15

Leu Asp

<210> SEQ ID NO 5
<211> LENGTH: 18
<212> TYPE: PRT
<213> ORGANISM: Homo sapiens

<400> SEQUENCE: 5

His Tyr Leu Pro Gly Ser His Arg Lys Val Ile Lys Asn Val Ala Glu
1               5                   10                  15

Val Lys

<210> SEQ ID NO 6
<211> LENGTH: 18
<212> TYPE: PRT
<213> ORGANISM: Homo sapiens

<400> SEQUENCE: 6

Ile Phe Arg Gly Tyr Leu Ile Pro Lys Gly Thr Val Trp Pro Thr Leu
1               5                   10                  15

Asp Ser

<210> SEQ ID NO 7
<211> LENGTH: 20
<212> TYPE: PRT

```
<213> ORGANISM: Homo sapiens

<400> SEQUENCE: 7

Phe Asn Asn Gly Pro Thr Trp Lys Asp Ile Arg Arg Phe Ser Leu Thr
1               5                   10                  15

Thr Leu Arg Asn
            20

<210> SEQ ID NO 8
<211> LENGTH: 20
<212> TYPE: PRT
<213> ORGANISM: Homo sapiens

<400> SEQUENCE: 8

Gly Pro Thr Trp Lys Asp Ile Arg Arg Phe Ser Leu Thr Thr Leu Arg
1               5                   10                  15

Asn Tyr Gly Met
            20

<210> SEQ ID NO 9
<211> LENGTH: 19
<212> TYPE: PRT
<213> ORGANISM: Homo sapiens

<400> SEQUENCE: 9

Trp Lys Asp Ile Arg Arg Phe Ser Leu Thr Thr Leu Arg Asn Tyr Gly
1               5                   10                  15

Met Gly Lys

<210> SEQ ID NO 10
<211> LENGTH: 21
<212> TYPE: PRT
<213> ORGANISM: Homo sapiens

<400> SEQUENCE: 10

Ile Arg Arg Phe Ser Leu Thr Thr Leu Arg Asn Tyr Gly Met Gly Lys
1               5                   10                  15

Gln Gly Asn Glu Ser
            20

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 11

His His His His His His
1               5
```